United States Patent
Oriakhi et al.

(10) Patent No.: US 7,422,713 B2
(45) Date of Patent: Sep. 9, 2008

(54) HYBRID ORGANIC-INORGANIC COMPOSITION FOR SOLID FREEFORM FABRICATION

(75) Inventors: Christopher Oriakhi, Corvallis, OR (US); Terry M. Lambright, Corvallis, OR (US); Vladek P Kasperchik, Corvallis, OR (US); David C Collins, Philomath, OR (US); Isaac Farr, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1083 days.

(21) Appl. No.: 10/686,423

(22) Filed: Oct. 14, 2003

(65) Prior Publication Data

US 2005/0082710 A1   Apr. 21, 2005

(51) Int. Cl.
   *B29C 67/00*   (2006.01)
(52) U.S. Cl. .................... 264/113; 264/308
(58) Field of Classification Search .............. None
   See application file for complete search history.

(56) References Cited

U.S. PATENT DOCUMENTS

| | | | |
|---|---|---|---|
| 3,814,717 A | 6/1974 | Wilson et al. | |
| 5,215,459 A | 6/1993 | Ney et al. | |
| 6,066,285 A | 5/2000 | Kumar | |
| 6,409,902 B1 | 6/2002 | Yang et al. | |
| 6,454,972 B1 | 9/2002 | Morisette et al. | |
| 6,742,456 B1 * | 6/2004 | Kasperchik et al. | 101/483 |
| 6,955,776 B1 | 10/2005 | Feenstra | |
| 2003/0114936 A1 | 6/2003 | Sherwood et al. | |

FOREIGN PATENT DOCUMENTS

| | | |
|---|---|---|
| JP | A-H2-164807 | 6/1990 |
| JP | A-H4-231962 | 8/1992 |
| JP | A-H6-99505 | 4/1994 |
| JP | A-H7-291691 | 11/1995 |
| JP | A-2002-527144 | 8/2002 |
| JP | A-2001-58357 | 6/2003 |
| WO | WO 02/064354 | 8/2002 |
| WO | WO 2004/043681 A2 | 5/2004 |

OTHER PUBLICATIONS

A.D. Wilson et al "The Glass-Ionomer Cement, a New Translucent Dental Filling Material", J. Appl. Chem. Biotechnol., 1971, V. 21, November, pp. 313.

* cited by examiner

*Primary Examiner*—Mary Lynn F Theisen

(57) ABSTRACT

A method for solid free-form fabrication of a three-dimensional object includes depositing a particulate blend in a defined region, the particulate blend including reactive glass ionomer particulates, cross-linkable polyacid particulates including polyvinyl pyrrolidone-co-polyacrylic acid, and nanocomposites, ink-jetting an aqueous phase binder onto a predetermined area of the particulate blend to form hydrated cement in the predetermined area, and hardening the hydrated cement.

17 Claims, 5 Drawing Sheets

HYBRID ORGANIC-INORGANIC COMPOSITION FOR SOLID FREEFORM FABRICATION

BACKGROUND

The efficient production of prototype three-dimensional compositions or objects can provide an effective means of reducing the time it takes to bring a product to market at a reasonable cost. A typical approach for preparing prototypes has required specific tooling, such as molds and dies, which can be a slow and cumbersome process.

Recently, computerized modeling has alleviated some of the need for building prototypes. Computer modeling can be carried out quickly and provide a good idea of what a product will look like without a specialized tooling requirement. However, the fabrication of a tangible object is still often preferred for prototyping. The merging of computer modeling and the physical formation of three-dimensional objects is sometimes referred to as solid freeform fabrication.

Solid freeform fabrication (SFF) is a process whereby three-dimensional objects, for example, prototype parts, models, working tools, production parts, molds, and other articles are manufactured by sequentially depositing layers of a structural material. Computer aided design (CAD) is commonly used to automate the design process. Using a suitable computer, an operator may design a three-dimensional article and then create that object by employing a positionable ejection head that selectively emits the structural material. Various techniques that employ SFF have been explored.

Traditional methods of forming SFF objects include using commercially available gypsum and biopolymer systems or acid-base cements. The gypsum and biopolymer system necessitates numerous hours to set and the final object has poor mechanical properties. Similarly, the acid-base cement method tends to produce final objects that have low fracture toughness, are sensitive to environmental changes such as humidity, and result in poor definition of the resulting SFF article's detail.

SUMMARY

A method for solid free-form fabrication of a three-dimensional object includes depositing a particulate blend in a defined region, the particulate blend including reactive glass ionomer particulates, cross-linkable polyacid particulates including polyvinyl pyrrolidone-co-polyacrylic acid, and nanocomposites, ink-jetting an aqueous phase binder onto a predetermined area of the particulate blend to form hydrated cement in the predetermined area, and hardening the hydrated cement.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

A method and apparatus for forming SFF articles with a hybrid organic-inorganic composition is described herein. More specifically, a cement-forming organic-inorganic complex powder system including inorganic phosphates, aluminosilicate glass, metal oxides, layered double hydroxides, organic monomers, polyacids, biopolymers and polymer-clay nanocomposites is incorporated with a reactive matrix-forming binder to create three-dimensional objects.

As used in the present specification and in the appended claims, the term "cement" is meant to be understood broadly as any building material that hardens to act as an adhesive. Similarly, "binder" is meant to be understood broadly as any material used to bind separate particles together or facilitate adhesion to a surface. Additionally, the term "substrate" is meant to be understood as any build platform, removable material, or previously deposited reactive or powder material. A "build platform" is typically a rigid substrate that is used to support deposited material from a SFF apparatus. Similarly, the term "curing" is meant to refer to the process of hardening or setting a substance to form a solid three dimensional object.

In the following description, for purposes of explanation, numerous specific details are set forth in order to provide a thorough understanding of the present system and method for forming SFF articles with a hybrid organic-inorganic composition. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
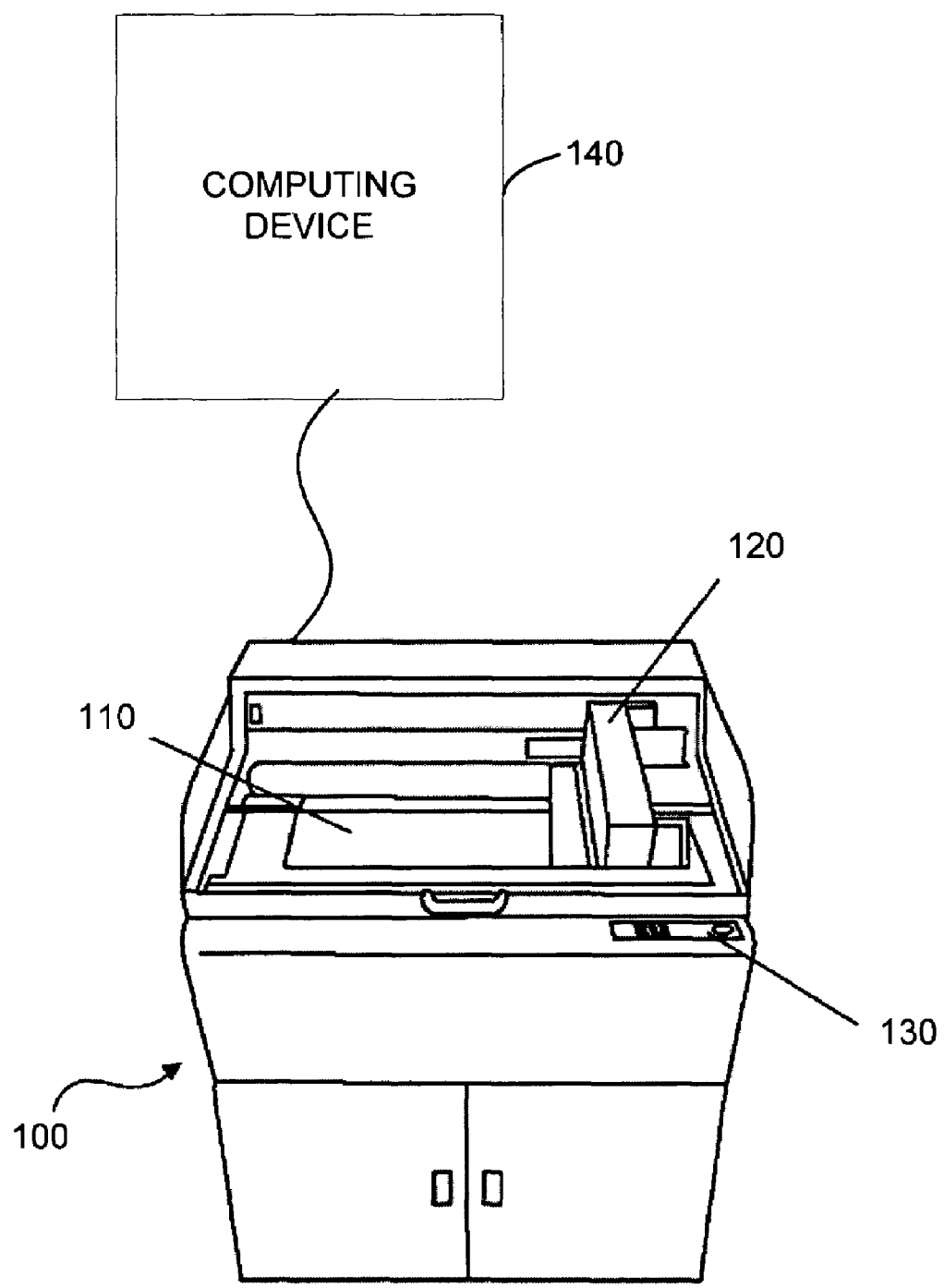
FIG. 1 is a perspective view of a SFF system that may be used to implement exemplary embodiments of the present system and method.

FIG. 1 illustrates a solid freeform fabrication (SFF) system (100) that may incorporate the present method of forming SFF articles with a hybrid organic-inorganic composition. As shown in FIG. 1, an SFF system may include a fabrication bin (110), a moveable stage (120), and a display panel (130) including a number of controls and displays. Additionally, a computing device (140) may be communicatively coupled to the SFF system (100).

The fabrication bin (110) shown in FIG. 1 may be configured to receive and facilitate the building of a desired three-dimensional object on a substrate. The building of the desired three-dimensional object may include the spreading of a powder and the selective dispensing of a binder into the powder. While the SFF system (100) illustrated in FIG. 1 is shown as a single, stand-alone, self-contained freeform fabrication system, the present powder based SFF system and methods may be incorporated into any freeform fabrication system that utilizes powder-based methods, regardless of the structure or configuration of the freeform fabrication system.

The moveable stage (120) of the SFF system (100) illustrated in FIG. 1 is a moveable material dispenser that may include any number of inkjet material dispensers configured to dispense liquid binder material. The moveable stage (120) may be controlled by a computing device (140) and may be controllably moved by, for example, a shaft system, a belt system, a chain system, etc. As the moveable stage (120) operates, the display panel (130) may inform a user of operating conditions as well as provide the user with a user interface.

As a desired three-dimensional object is formed, the computing device (140) may controllably position the moveable stage (120) and direct one or more of the dispensers (not shown) to controllably dispense liquid binder material at predetermined locations within the fabrication bin (110) thereby forming a desired three-dimensional object. The inkjet material dispensers used by the SFF system (100) may be any type of inkjet dispenser configured to perform the present method including, but in no way limited to thermally actuated inkjet dispensers, mechanically actuated inkjet dispensers, electrostatically actuated inkjet dispensers, magnetically actuated dispensers, piezoelectrically actuated dispensers, continuous inkjet dispensers, etc. Additionally, the ink-jet printhead dispenser can be heated to assist in dispensing viscous chemical compositions. A more demonstrative cross-sectional view of the SFF apparatus of FIG. 1 is presented in FIG. 2.

Figure 2:
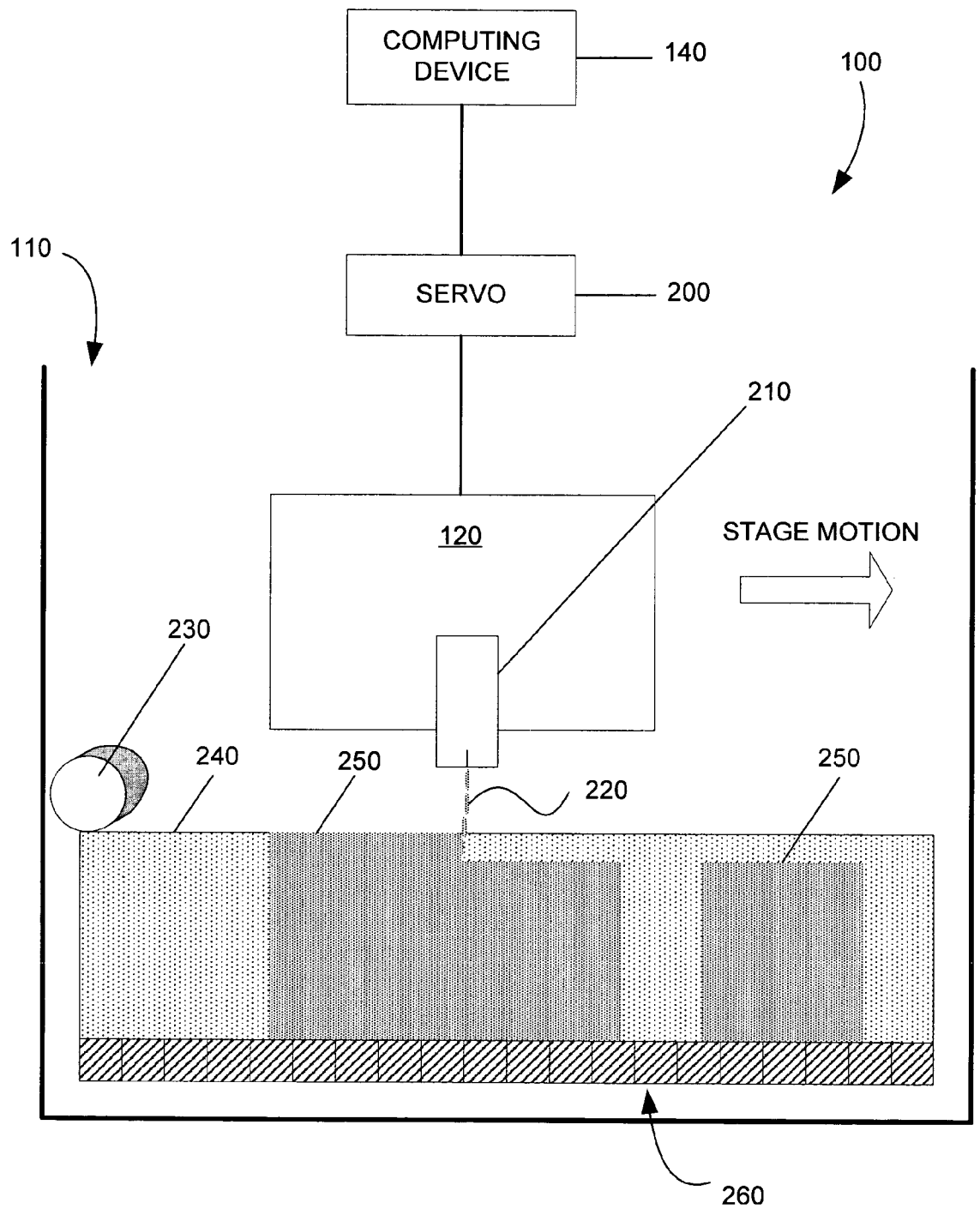
FIG. 2 is a cross-sectional view of a SFF system that may be used to implement exemplary embodiments of the present system and method.

As shown in FIG. 2, the computing device (140) may be communicatively coupled to a servo mechanism (200). The computing device (140) may communicate commands to the servo mechanism (200) causing it to selectively position the moveable stage (120). One or more inkjet dispensers (210) may be coupled to the moveable stage (120) and to a number of material reservoirs (not shown). Once positioned by the servo mechanism (200), the inkjet dispenser (210) may eject a reactive matrix-forming binder (220) supplied by the material reservoir. The liquid phase binder (220) that is stored in the material reservoir (not shown) and supplied to the inkjet dispenser (210) to be dispensed may include phosphoric acid, phytic acid, citric acid, tartaric acid, and other organic hydroxy acids with complexing properties as well as dye colorants, pigment colorants, pyrrolidone, 1,5-hexanediol, low molecular weight water-soluble ethylene oxide-propylene oxide oligomers, surfynol 465, and/or water. The advantages and reactions of the liquid phase binder (220) will be described in detail below with reference to FIGS. 2 through 4D.

FIG. 2 also illustrates the components of the present system that may be used to receive the liquid phase binder (220) and aid in the formation of a desired three-dimensional object. As shown in FIG. 2, the fabrication bin (110) of the SFF system (100) may include a substrate (260) having a cement-forming organic-inorganic complex powder (240) disposed thereon. According to one exemplary embodiment, the cement-forming organic-inorganic complex powder (240) may be dispensed onto the substrate (260) in bulk quantities from a powder reservoir (not shown) and planarized to a desired thickness with the use of a mechanical roller (230). The cement-forming organic-inorganic complex powder (240) may be spread from 0.005 millimeter to over 1 millimeter thick depending on the powder sizes employed. Control of the mechanical roller (230) may be performed by the servo mechanism (200) to controllably deposit and planarize the cement-forming organic-inorganic complex powder (240) on the substrate (260). The cement-forming organic-inorganic complex powder (240) dispensed onto the substrate includes some or all of the following: a reactive glass powder plus an ionomer, cross-linkable polyacids, pH-modifiers, nanocomposites, biomolecules, Al(3+) sources, and/or Zn(2+) sources. Composition, interaction, and functions of the components of the cement-forming organic-inorganic complex powder (240) will be described in further detail below with reference to FIGS. 2 through 4D.

Once the liquid phase binder (220) is dispensed in the layer of cement-forming organic-inorganic complex powder (240), a mixture (250) of liquid phase binder (220) and cement-forming organic-inorganic complex powder (240) exists on the substrate (260) defining a desired three-dimensional object. The system and method for using the SFF system (100) illustrated in FIG. 2 will be described in detail below with reference to FIG. 3 through FIG. 4D.

Exemplary Compositions

As shown in FIG. 2, the present system and method for operating an SFF system (100) while incorporating a cement-forming organic-inorganic complex powder includes the combination of a cement-forming organic-inorganic complex powder (240) with a liquid phase binder (220). Exemplary compositions of the cement-forming organic-inorganic complex powder (240) and the liquid phase binder will be given herein.

As stated previously, the liquid phase binder (220) stored in the material reservoir (not shown) and supplied to the inkjet dispenser (210) to be dispensed may include phosphoric acid, phytic acid, citric acid or other hydroxy acids, dye colorants, pigment colorants, pyrrolidone, 1,5-hexanediol, low molecular weight water-soluble ethylene oxide-propylene oxide oligomers, surfynol 465, and/or water.

Water may form a large part of the liquid phase binder (220). Water may be used due to its low cost, reactivity, jettability, and efficiency in wetting cement forming powders.

The liquid phase binder (220) illustrated in FIG. 2 is also jettable from an inkjet dispenser. While a liquid binder of water alone is jettable, it is jetted inefficiently. The present liquid phase binder (220) is aqueous based but due to the added reactive components, the following are also typically added to improve jettability: surfactants and viscosity modifiers including, but in no way limited to, surfynol 465.

Solution pH-modifiers may also be added to the liquid phase binder (220) in order to decrease the pH of the system which subsequently increases the rate of reaction and decreases the curing time of the resulting three-dimensional object. Additionally, the inclusion of citric acid will also enhance the mechanical properties of the resulting three-dimensional object. The mechanical properties of the resulting three-dimensional object will be enhanced when the citric acid interacts with multivalent inorganics that may be present in the cement-forming organic-inorganic complex powder as described below. The pH modifiers included in the present liquid phase binder include, but are in no way limited to, phosphoric acid, phytic acid, and citric acid or other hydroxy acids.

2-pyrrolidone is a solvent that may also be included in the liquid phase binder (220). 2-pyrrolidone is efficient in dissolving many polymers and other materials. 2-pyrrolidone is also a good co-solvent for many water-soluble dyes which could be present in the binder. Moreover, 2-pyrrolidone is also an example of a humectant and de-capping agent that may be included in the liquid phase binder (220) to prevent inkjet nozzles from clogging upon water evaporation. Other examples of humectants and de-capping agents include, but are in no way limited to, 1,5-hexanediol, di- and tri-functional alcohols, or low molecular weight water-soluble ethylene oxide-propylene oxide oligomers. The low molecular weight water-soluble ethylene oxide-propylene oxide oligomers may also modify viscosity and wetting behavior of the liquid phase binder (220).

Additionally, dye colorants and pigment colorants may be added to the liquid phase binder (220) in order to produce a three-dimensional object of one or more colors. The dye colorants and pigment colorants may be a single color equally distributed in the liquid phase binder (220), or it may be multiple colors housed in separate material reservoirs (not shown).

FIG. 2 also illustrates the cement-forming organic-inorganic complex powder (240). The cement-forming organic-inorganic complex powder (240) dispensed onto the substrate includes a reactive glass combined with some or all of the following: cross-linkable polyacids, pH modifiers, nanocomposites, biomolecules, Al(3+) sources, and/or Zn(2+) sources.

The base component of the cement-forming organic-inorganic complex powder (240) illustrated in FIG. 2 is the reactive glass. The reactive glass, once in contact with the binder material, releases cross-linking components Ca(2+) and Al(3+). Once these cross-linking components are released from the reactive glass, they are free to react with acidic groups in the binder/powder mix Once the cross-linking components released from the reactive glass reacts with the acidic groups (such as polyacids mentioned below), a cross-link occurs and the shape of the desired three-dimensional object is set. Examples of reactive glass that may be included in the present cement-forming organic-inorganic complex powder (240) include, but are in no way limited to, reactive glass or ion-leachable calcium aluminosilicates very often containing fluoride.

As noted above, cross-linkable polyacids are also included in the present cement-forming organic-inorganic complex powder (240) to react with cross-linking components released from the reactive glass. The cross-linkable polyacids that may be included in the present cement-forming organic-inorganic complex powder (240) include, but are in no way limited to, polyacrylic acid (PAA), polygalaturonic acid, polyethelyne-co-maleic acid and other polycarboxylic acids as well as unsaturated carboxylic acids co-polymers with other polymerizable species.

Polyvinyl pyrrolidone-co-polyacrylic acid (PVP-co-PAA) is also included in the present cement forming organic-inorganic complex powder (240). Polyvinyl pyrrolidone-co-polyacrylic acid (PVP-co-PAA) is a cross-linkable polyacid that may be cross-linked into the glass-ionomer network mentioned above. Additionally, the inclusion of PVP-co-PAA into the cement-forming organic-inorganic complex powder (240) may also enhance working time and mechanical properties of the resulting three-dimensional object.

pH modifiers may also be added to the cement-forming organic-inorganic complex powder (240) in order to decrease the pH of the system which subsequently increases the rate of reaction and decreases the curing time of the resulting three-dimensional object. Additionally, the inclusion of citric acid will also enhance the mechanical properties of the resulting three-dimensional object. The mechanical properties of the resulting three-dimensional object will be enhanced when the citric acid interacts with the multivalent inorganics that may be present in the layered double hydroxides (LDH) also contained in the cement-forming organic-inorganic complex powder as described below. The pH modifiers included in the present cement-forming organic-inorganic complex powder (240) include, but are in no way limited to: tartaric acid, citric acid, glutamic acid, diglycolic acid, DL aspartic acid, iminodiacetic acid, itaconic acid, and/or phosphoric acid salts such as $NH_4H_2PO_4$.

Nanocomposites may also be included in the present cement-forming organic-inorganic complex powder (240) including, but in no way limited to, PEO/clay nanocomposites, closite 10A, dosite 30B, closite Na+, hydrophilic polymer-silicate nanocomposites, hydroxyapatite, and/or layered double hydroxide (LDH) nanocomposites. Typical nanocomposites act as reinforcing agents and moisture reservoirs in the desired three-dimensional object to both add structural support and to prevent moisture loss which may result in drying or cracking of the produced three-dimensional object.

Layered double hydroxide (LDH) nanocomposites are also included in the present cement-forming organic-inorganic complex powder (240) to not only act as a reinforcing agent, but also to enhance the mechanical properties of the resulting three-dimensional object. LDHs are nanocomposites comprised of multivalent cationic inorganics such as aluminum, calcium, magnesium, zinc, etc. which have intercalated anions such as nitrate, carbonate, sulfate, or polyanions. The LDHs provide additional metal sites which serve as crosslinker for polyacids and also serve the function of nanocomposite fillers as reinforcing agents.

Hydroxyapatite, listed above in the list of nanocomposites, serves more as a nanofiller in the present system because it does not act as a moisture reservoir to prevent moisture loss. Rather, the hydroxyapatite merely acts as a reinforcing agent in the resulting three-dimensional object.

Biomolecules may also be added to the cement-forming organic-inorganic complex powder (240). Biomolecules are water soluble and may act as a thickening agent or adhesive to enhance the mechanical properties of the resulting three-dimensional object. Types of biomolecules that may form part of the cement-forming organic-inorganic complex powder include, but are in no way limited to, dextrin and soluble starch.

Additionally, Al(3+) sources and Zn(2+) sources may be added to the cement-forming organic-inorganic complex powder (240) illustrated in FIG. 2. Examples of Al(3+) sources and Zn(2+) sources may include, but are in no way limited to, $Al(NO_3)_3$ and ZnO. The addition of Al(3+) sources and Zn(2+) sources are basic components which will crosslink with the above-mentioned polyacids thereby enhancing the physical properties of the resulting three-dimensional object.

The above-mentioned components of the cement-forming organic-inorganic complex powder (240) may be combined in a number of formulations to produce a desired three-dimensional object when combined with the liquid phase binder (220). The present system and method include, but are in no way limited to, the formulations listed below.

A first exemplary formulation for the cement-forming organic-inorganic complex powder (240) includes 75 wt % reactive glass, 10 wt % PAA (MW 60K), 5 wt % tartaric acid, 2.5 wt % citric acid, 2.5 wt % polyethylene oxide (PEO)/day nanocomposites, and 5 wt % $Al(NO_3)_3$.

A second exemplary formulation for the cement-forming organic-inorganic complex powder (240) includes 80 wt % reactive glass, 5 wt % PAA (MW 60K), 5 wt % glutamic acid, 2.5 wt % diglycolic acid, 2.5 wt % polyethylene oxide (PEO)/day nanocomposites, and 5 wt % Dextrin.

A third exemplary formulation for the cement-forming organic-inorganic complex powder (240) includes 75 wt % reactive glass, 10 wt % polygalaturonic acid, 5 wt % DL aspartic acid, 2.5 wt % citric acid, 2.5 wt % polyethylene oxide (PEO)/clay nanocomposites, and 5 wt % hydroxyapatite.

A fourth exemplary formulation for the cement-forming organic-inorganic complex powder (240) includes 70 wt % reactive glass, 10 wt % zinc oxide (ZnO), 10 wt % PE-co-maleic acid, 3 wt % citric acid, 3 wt % iminodiacetic acid, 2 wt % soluble starch, and 2 wt % Closite 10A.

A fifth exemplary formulation for the cement-forming organic-inorganic complex powder (240) includes 60 wt % reactive glass, 20 wt % (NH4)H2PO4, 5 wt % PAA (MW 60K), 5 wt % polygalaturonic acid, 5 wt % iminodiacetic acid, and 5 wt % Closite 10A.

A sixth exemplary formulation for the cement-forming organic-inorganic complex powder (240) includes 75 wt % reactive glass, 8 wt % itaconic acid, 10 wt % PE-co-maleic acid, 2 wt % citric acid, 2 wt % soluble starch, and 3 wt % Closite 30B.

A seventh exemplary formulation for the cement-forming organic-inorganic complex powder (240) includes 75 wt % reactive glass, 10 wt % PVP-co-PAA, 8 wt % itaconic acid, 3 wt % Closite Na+, 2 wt % citric acid, and 2 wt % soluble starch.

An eighth exemplary formulation for the cement-forming organic-inorganic complex powder (240) includes 75 wt % reactive glass, 8 wt % itaconic acid, 10 wt % PVP-co-PAA, 2 wt % citric acid, 2 wt % soluble starch, and 3 wt % Closite 30B.

The present system and method is in no way limited to the above mentioned exemplary formulations. The formulations have merely been presented here for illustrative purposes only.

Exemplary Implementation and Operation

Figure 3:
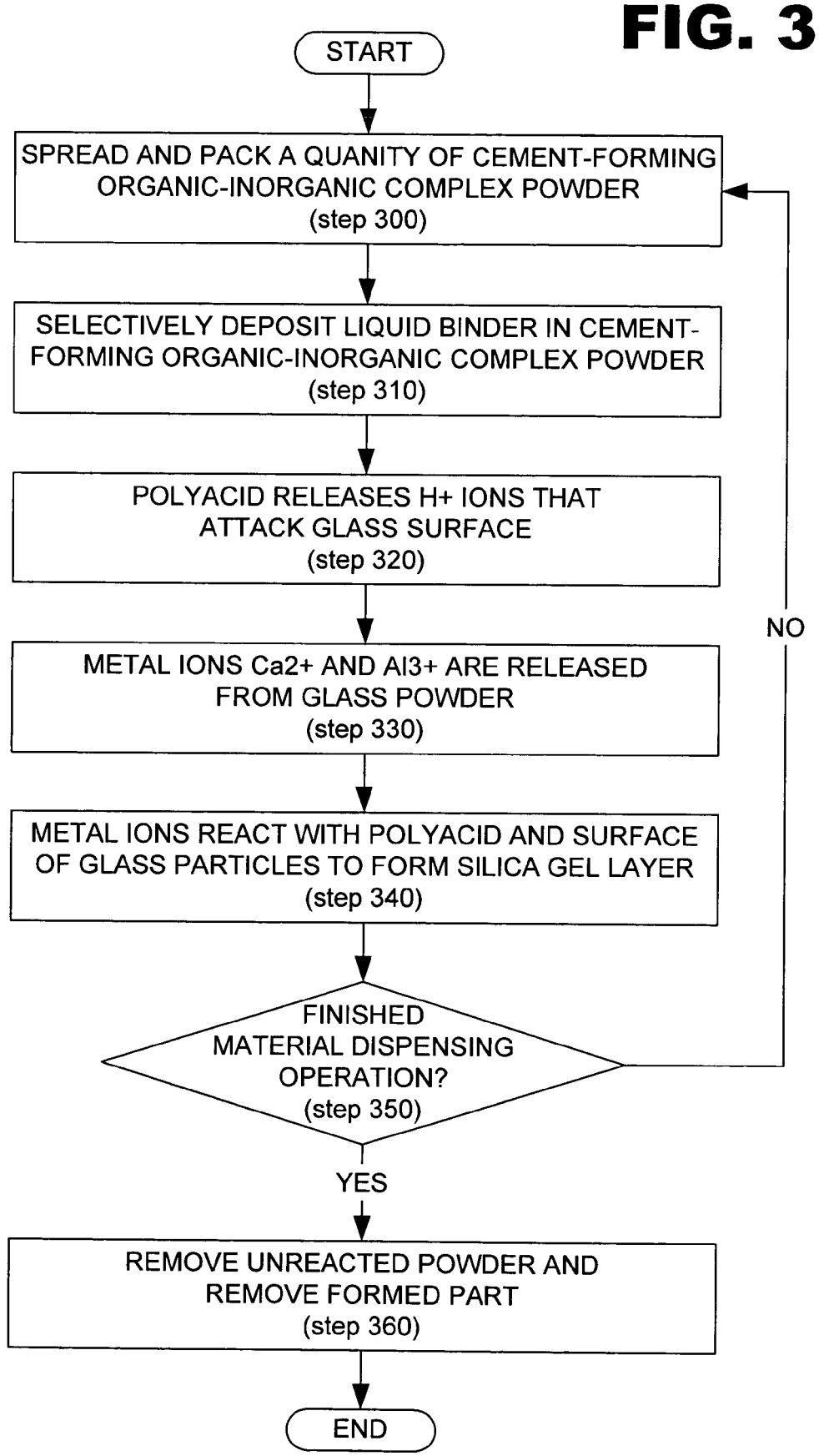
FIG. 3 is a flow chart illustrating a method for performing the present method using a one-part reactive material according to one exemplary embodiment.

FIG. 3 is a flow chart illustrating a method for operating the SFF system (100; FIG. 2) illustrated in FIG. 2 while incorporating a cement-forming organic-inorganic complex powder (240; FIG. 2) according to one exemplary embodiment. While FIG. 3 illustrates the likely mechanism for operating an SFF system while incorporating a cement-forming organic inorganic complex powder, the present system and method are in no way limited strictly to the embodiment illustrated in FIG. 3. As shown in FIG. 3, the present exemplary method begins by spreading and packing a specified quantity of cement-forming organic-inorganic complex powder (step 300). Once a specified quantity of cement forming organic-inorganic complex powder has been spread, the SFF system (100; FIG. 2) selectively deposits a specified quantity of liquid binder into the cement-forming organic-inorganic complex powder (step 310). Once the cement-forming organic-inorganic complex powder and the liquid binder combine, a polyacid in the binder contacts the reactive glass and subsequently attacks the glass surfaces with released hydrogen ions (step 320). When attacked by the hydrogen ions, the glass surfaces release multivalent cationic species (step 330) which in turn react with the polyacid and the surface of the glass particles to form a silica gel layer (step 340). With the silica gel layer formed, a number of reactions take place to further solidify the desired three-dimensional object (step 345) and the SFF system (100; FIG. 2) determines whether it has finished the material dispensing operation (step 350). If the material dispensing operation is complete (YES, step 350), unreacted cement-forming organic-inorganic complex powder is removed from the formed part (step 360) and the formation process is complete. If, however, the SFF system (100; FIG. 2) determines that it has not finished the material dispensing operation (NO, step 350), the SFF system returns again to step 300 and spreads and packs another quantity of cement-forming organic-inorganic complex powder (step 300) in preparation of performing another binder deposition. The above-mentioned process will now be described in detail with reference to FIG. 4A through FIG. 4D.

As depicted in FIG. 3, the present system and method begins by spreading and packing a quantity of cement-forming organic-inorganic complex powder (step 300). FIG. 4 illustrates a quantity of cement-forming organic-inorganic complex powder (400) that has been spread and packed on a substrate (260). The minimum amount of powder (400) that may be spread is governed primarily by the powder size. According to one exemplary embodiment, the powder may be spread to a thickness from 0.005 millimeter to over 1 millimeter. As mentioned previously, the cement-forming organic-inorganic complex powder (400) includes a reactive glass ionomer and some or all of the following: cross-linkable polyacids, pH modifiers, nanocomposites, biomolecules, Al(3+) sources, and/or Zn(2+) sources.

Figure 4A:
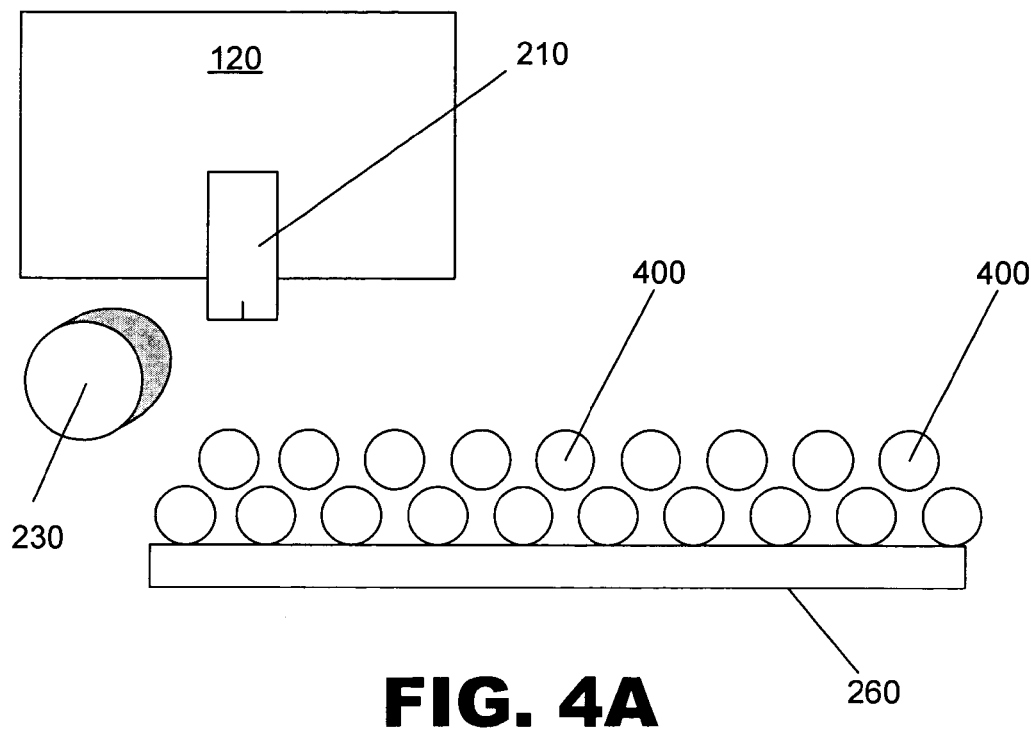
FIG. 4A is a cross-sectional view illustrating a powder that may be used by the present method according to one exemplary embodiment.
Figure 4B:
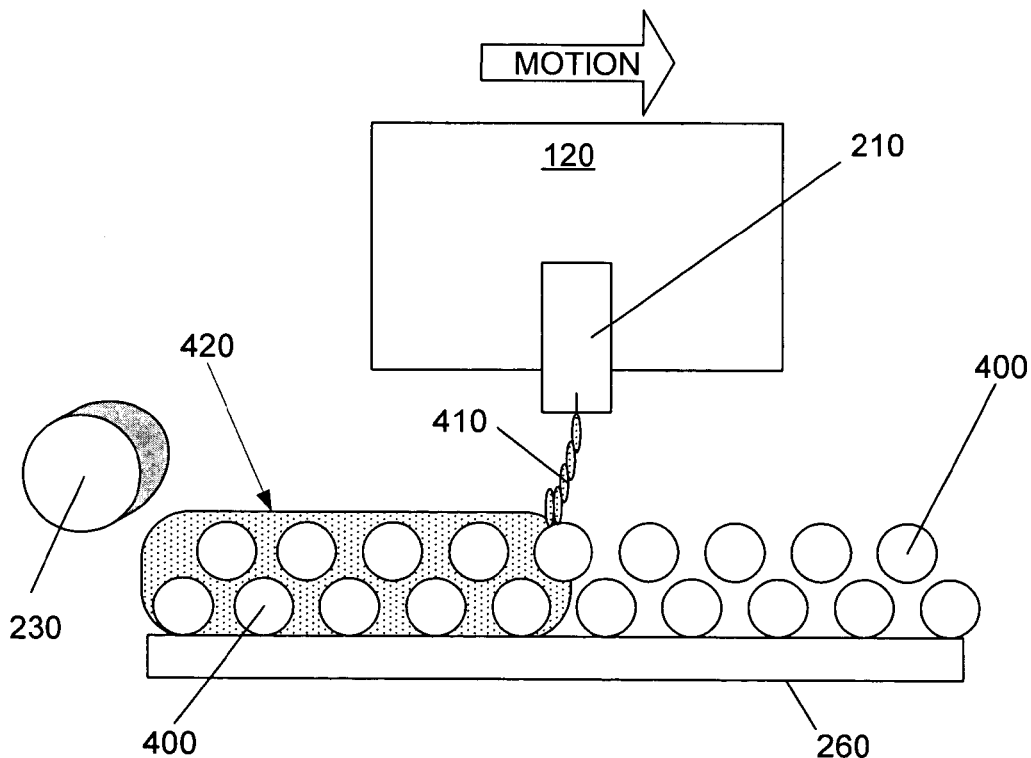
FIG. 4B is a cross-sectional view showing the deposition of a one-part reactive material according to one exemplary embodiment.

Once the cement-forming organic-inorganic complex powder has been spread (step 300; FIG. 3), the moveable stage (120) may selectively deposit liquid phase binder into the cement-forming organic-inorganic complex powder (step 310; FIG. 3). As shown in FIG. 4B, the moveable stage (120) may be controllably positioned by the computing device (140; FIG. 1) and then caused to controllably deposit quantities (410) of the liquid phase binder (420) into the cement-forming organic-inorganic complex powder (400). The locations where the quantities (410) of the liquid phase binder (420) will be deposited are determined by the CAD or other computer modeling program directing the formation of the desired three-dimensional object. Once deposited, the locations containing liquid phase binder (420) will define the boundaries of the resulting three-dimensional object.

The amount of liquid phase binder that is deposited into the cement-forming organic-inorganic complex powder is typically calculated as a ratio of binder to powder. For the present system and method, the ratio of binder to powder may range from approximately 0.05:1 to 0.5:1.

When the cement-forming organic-inorganic complex powder (400) and the liquid phase binder (420) have been combined, a "glass-ionomer" chemical reaction takes place to serve as a rigid quick-setting foundation for the resulting three-dimensional object. First, once the glass powder and acid or polyacid components are mixed, polyacids release positively charged hydrogen ions that contact the surface of the reactive glass contained in the cement-forming organic-inorganic complex powder (step 320; FIG. 3). Once the positively charged hydrogen ions attack the reactive glass, cross-linking metal ions such as Ca2+ and Al3+ are released from the reactive glass (step 330; FIG. 3). The metal ions Ca2+ and Al3+, which are released from the glass following the release of H+, react with the polyacid and the surface of the glass particles to form a silica gel layer (step 340; FIG. 3). This glass-ionomer chemical reaction provides a quick setting and relatively high strength "green object" or one which is not yet fully cured.

Figure 4C:
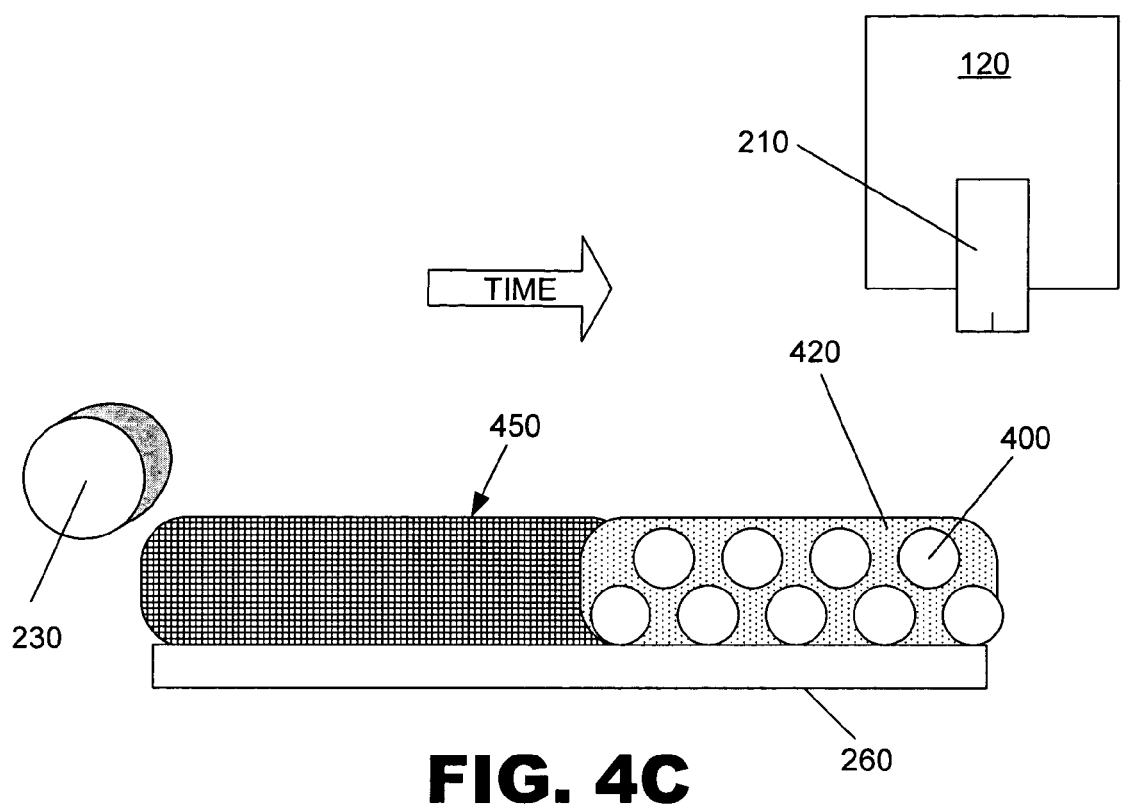
FIG. 4C is a cross-sectional view showing the curing process with the passing of time according to one exemplary embodiment.

Once the glass-ionomer chemical reaction has occurred, additional materials and reactions take place to further aid in solidifying the three-dimensional object (step 345). FIG. 4C illustrates that as time passes (indicated by arrow), the chemical reactions take place and the mixture of cement-forming organic-inorganic complex powder (400) and liquid phase binder (420) combine to form a structural build material (450).

The material properties of the structural build material (450) are enhanced over typical glass ionomer substances due, at least in part, to the additional materials contained in the cement-forming organic-inorganic complex powder (400). First, the use of polyvinyl pyrrolidone or its copolymer(s) and nanocomposites derived from it offer unique water retention characteristics. Secondly, the addition of layered double hydroxides (LDH) to the cement-forming organic-inorganic complex powder (400) provides additional metal sites, which serve as crosslinker for polyacids and also serve the function of nanocompoiste fillers or reinforcing agents. These nanocomposites derived from layered double hydroxide may improve the mechanical properties of the resulting three-dimensional object by serving as crack-propagation traps. During gelation or the formation of the network structure, the polymer-clay nanocomposites fillers in the mix are dispersed or trapped within the matrix. The silicate layer in the clay nanocomposites are only a few nanometers thick and should provide uniform nanometer-level dispersion. Uniform dispersion of the nanofillers should enhance interfacial interaction and hence the mechanical properties of the resulting solid. The degree of reinforcement provided by the nanocomposites depends on the rigidity and the aspect ratio of the fillers and the adhesive strength between the filler and the polymer/glass matrix. Third, the other nanocomposites mentioned above may serve as reinforcing agents and moisture reservoirs in the resulting object. This will prevent moisture loss in the resulting three-dimensional object reducing the likelihood of drying or cracking. Fourth, the addition of citric and other acids decrease the pH of the overall system. This results in an increased rate of reaction as well as enhanced mechanical properties. Additionally, mechanical properties will be enhanced because the citric acid will interact with the multivalent inorganics present in the layered double hydroxides (LDH). Fifth, the addition of zinc oxide (ZnO) may crosslink with the polyacids in the system to further enhance the mechanical properties of the resulting three-dimensional object.

As the above-mentioned reactions take place, the formed article further solidifies the desired three-dimensional object (step 345). While step 345 may suggest that the mixture of cement-forming organic-inorganic complex powder (400) and liquid phase binder (420) is completely hardened before the next layer of powder is spread; this is not the case. In some instances, the complete hardening of the mixture takes days while the initial hardening takes minutes. The initial hardening or curing sufficiently cures the mixture to support the spreading of a subsequent layer of cement-forming organic-inorganic complex powder (400). Subsequent layers of cement-forming organic-inorganic complex powder (400) may be spread about every 15 seconds to 3 minutes.

Figure 4D:
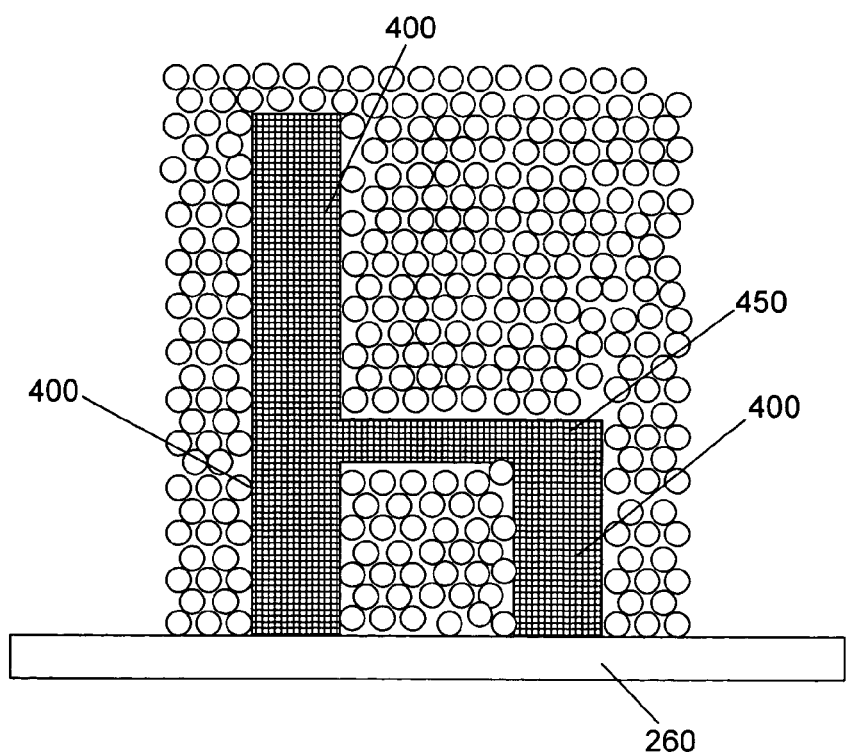
FIG. 4D is a cross-sectional view illustrating an object formed by the present method according to one exemplary embodiment.

Upon formation, the computing device then determines whether it has completed the desired material dispensing operation (step 350). If the formation of the desired three-dimensional object has been completed (YES, step 350), then the formed object is isolated by removing the unreacted powder and extracting the part (step 360). If, however, the computing device determines that the desired three-dimensional object has not yet been satisfactorily formed (NO, step 350), the SFF system (100; FIG. 1) again spreads and packs a quantity of cement-forming organic-inorganic complex powder (step 300) and repeats the above-mentioned process. FIG. 4D illustrates a completed three-dimensional object composed of structural build material (450). As shown in FIG. 4D, the completed three-dimensional object may, but is not required to, be formed by multiple iterations of the above-mentioned method.

In conclusion, the present SFF system and method effectively provide a glass-ionomer based SFF system with enhanced mechanical properties. More specifically, the addition of polyvinyl pyrrolidone-co-polyacrylic acid, layered double hydroxides (LDH), and nanocomposites enhance working time and improve mechanical properties of the resulting SFF article. Examples of the improved mechanical properties include increased mechanical strength and fracture toughness when compared to traditional glass-ionomer articles and reduced moisture loss and dry-cracking in low humidity environments due to moisture reservoirs. Moreover, the present method and system may quickly produce a three-dimensional object by providing the powder in bulk while eliminating the need to form support structures.

The preceding description has been presented only to illustrate and describe exemplary embodiments of the system and method. It is not intended to be exhaustive or to limit the system and method to any precise form disclosed. Many modifications and variations are possible in light of the above teaching. It is intended that the scope of the system and method be defining by the following claims.

What is claimed is:

1. A method for solid free-form fabrication of a three-dimensional object, comprising:
   depositing a particulate blend in a defined region, said particulate blend including reactive glass ionomer particulates, cross-linkable polyacid particulates including polyvinyl pyrrolidone-co-polyacrylic acid, and nanocomposites;
   ink-jetting an aqueous phase binder onto a predetermined area of said particulate blend to form hydrated cement in said predetermined area; and
   hardening said hydrated cement.

2. The method of claim 1, further comprising removing a portion of said particulate blend that does not form said hydrated cement.

3. The method of claim 1, wherein said reactive glass ionomer particulates comprise a glass ionomer cement.

4. The method of claim 1, wherein said cross-linkable polyacid particulates comprise a polyvinyl pyrrolidone-co-polyacrylic acid and one of a polyacrylic acid, a polygalaturonic acid, a polyethelyne-co-maleic acid.

5. The method of claim 1, wherein said nanocomposites comprise one of PEO/clay nanocomposites, hydrophilic polymer-silicate nanocomposites, hydroxyapatite nanocomposites, or layered double hydroxide (LDH) nanocomposites.

6. The method of claim 1, wherein said particulate blend further comprises a source of $Al^{3+}$.

7. The method of claim 1, wherein said particulate blend further comprises a source of $Zn^{2+}$.

8. The method of claim 1, wherein said particulate blend further comprises biomolecules.

9. The method of claim 8, wherein said biomolecules comprise dextrin or soluble starch.

10. The method of claim 1, wherein said particulate blend further comprises a nanofiller.

11. The method of claim 10, wherein said nanofiller comprises hydroxyapatite.

12. The method of claim 1, wherein said step of hardening said cement is accelerated by including a pH modifier in said particulate blend.

13. The method of claim 12, wherein said pH modifier comprises one of tartaric acid, citric acid, glutamic acid, diglycolic acid, DL aspartic acid, iminodiacetic acid, itaconic acid, or $NH_4H_2PO_4$.

14. The method of claim 1, wherein said aqueous binder comprises a pH modifier to accelerate hardening said cement.

15. The method of claim 14, wherein said pH modifier comprises one of phosphoric acid, phytic acid or citric acid.

16. The method of claim 1, wherein said aqueous binder comprises colorants.

17. The method of claim 1, wherein said aqueous binder comprises phytic acid, citric acid, dye colorants, pigment colorants, pyrrolidone, 1,5-hexanediol, low molecular weight water-soluble ethylene oxide-propylene oxide oligomers, and water.

* * * * *

UNITED STATES PATENT AND TRADEMARK OFFICE
CERTIFICATE OF CORRECTION

| | |
|---|---|
| PATENT NO. | : 7,422,713 B2 |
| APPLICATION NO. | : 10/686423 |
| DATED | : September 9, 2008 |
| INVENTOR(S) | : Christopher Oriakhi et al. |

Page 1 of 1

It is certified that error appears in the above-identified patent and that said Letters Patent is hereby corrected as shown below:

In column 6, line 10, delete "dosite 30B" and insert -- closite 30B --, therefor.

In column 6, line 59, delete "(PEO)/day" and insert -- (PEO)/clay --, therefor.

In column 6, lines 64-65, delete "(PEO)/day" and insert -- (PEO)/clay --, therefor.

Signed and Sealed this

Twelfth Day of May, 2009

JOHN DOLL
*Acting Director of the United States Patent and Trademark Office*